(12) United States Patent
Takai et al.

(10) Patent No.: US 6,383,441 B1
(45) Date of Patent: May 7, 2002

(54) LIQUID-PERMEABLE TOPSHEET FOR BODY FLUIDS ABSORBENT ARTICLE AND METHOD OF MAKING THIS TOPSHEET

(75) Inventors: Hisashi Takai; Tomoko Tsuji; Hiroki Goda, all of Kagawa (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/545,404

(22) Filed: Apr. 7, 2000

Related U.S. Application Data

(62) Division of application No. 09/158,444, filed on Sep. 22, 1998, now Pat. No. 6,093,871.

(30) Foreign Application Priority Data

Sep. 22, 1997 (JP) .............................. 9-257160

(51) Int. Cl.$^7$ .............................. A61F 13/511
(52) U.S. Cl. .................. 264/557; 264/570; 264/119
(58) Field of Search .................. 264/119, 109, 264/518, 118, 557, 570

(56) References Cited

U.S. PATENT DOCUMENTS

| | | | |
|---|---|---|---|
| 3,814,101 A | 6/1974 | Kozak | 604/383 |
| 5,238,644 A | * 8/1993 | Boulanger et al. | 264/119 |
| 5,656,232 A | * 8/1997 | Takai et al. | 156/167 |

FOREIGN PATENT DOCUMENTS

| | | |
|---|---|---|
| EP | 0 313 766 A | 5/1989 |
| GB | 2 014 508 A | 8/1979 |
| GB | 2 284 786 A | 6/1995 |
| WO | WO 96/02215 A | 2/1996 |

* cited by examiner

Primary Examiner—Mary Lynn Theisen
(74) Attorney, Agent, or Firm—Baker & Daniels

(57) ABSTRACT

A topsheet for body fluids absorbent article is made of thermoplastic synthetic fibers mechanically entangled so as to extend substantially in a desired one direction and formed with liquid-permeable openings. The openings comprise a first group of openings each having a substantially oval shape defined by its major axis extending substantially in parallel to the direction in which the fibers extend and its minor axis extending orthogonally to the major axis and a second group of openings each having a substantially oval shape defined by its minor axis extending substantially in parallel to the direction in which the fibers 11 extend and its major axis extending orthogonally to the minor axis.

7 Claims, 5 Drawing Sheets

LIQUID-PERMEABLE TOPSHEET FOR BODY FLUIDS ABSORBENT ARTICLE AND METHOD OF MAKING THIS TOPSHEET

This is a Divisional of application Ser. No. 09/158,444, filed Sep. 22, 1998, now U.S. Pat. No. 6,093,871.

BACKGROUND OF THE INVENTION

This invention relates to a topsheet for a body fluids absorbent article such as a sanitary napkin or a disposable diaper and also to a method of making this topsheet.

It is well known to make a nonwoven fabric by subjecting a web of thermoplastic synthetic resin staple fibers each having a length of 20~70 mm to water jet streams of high pressure so that the fibers may be mechanically entangled and simultaneously liquid-permeable openings may be formed. The nonwoven fabric obtained in this manner can be used as the liquid-permeable topsheet of a sanitary napkin, a disposable diaper or the like. By such a method, the staple fibers tend to extend in parallel one to another along the direction in which the web travels. Consequently, the staple fibers extend closely in parallel one to another particularly along peripheral edges of the respective openings. These staple fibers thereby define correspondingly clear contours of the respective openings so far as these openings are oval openings each having a major axis extending along the direction in which the web travels and a minor axis extending orthogonally to the direction.

FIG. 8 shows an example of the porous nonwoven fabric 101 obtained by the above-mentioned method. As shown, the nonwoven fabric is formed with a plurality of oval openings 102 each having a major axis A—A extending in one direction and a minor axis B—B extending in the direction orthogonal to the major axis A—A. It is now assumed that the nonwoven fabric 101 is pulled, for example, in the proximity of one (102a) of the openings 102 in the direction of the major axis A—A. A dimension of this opening 102a as measured in the direction of its major axis A—A is enlarged while a dimension thereof in the direction of its minor axis B—B is reduced, with a result that this opening 102a may be deformed narrower as indicated by imaginary lines. If many of the openings 102 are deformed narrower like the opening 102a with their dimensions in the direction of their minor axes B—B extremely reduced, the nonwoven fabric 101 can not satisfy its desired function. This is for the reason that the openings 102 can no more smoothly guide body fluids and a time during which the body fluids stay on the topsheet, creating a discomfortable feeling of wetness against a wearer of the article.

SUMMARY OF THE INVENTION

In view of the above problem, it is a object of the invention to provide a topsheet used in body fluids absorbent article so improved that a body fluid permeability is never affected even if the topsheet is pulled in either direction thereof.

The object set forth above is achieved, according to one aspect of the invention, by a liquid-permeable topsheet forming at least a part of body fluids absorbent article, the topsheet comprising: the topsheet having skin-contacting side and skin-noncontactable side intended to and not to come in contact with the skin of a wearer of the article, respectively, the topsheet being formed by a nonwoven fabric made of thermoplastic synthetic fibers each having a fineness of 0.1~10 deniers and a length of 20~70 mm and mechanically entangled so as to extend in parallel one to another substantially in one direction and to leave a plurality of liquid-permeable openings providing a total area larger than a total area provided by interstices of the entangled fibers; and the openings including a first group of openings each having a substantially oval shape defined by a major axis thereof extending substantially in parallel to the one direction and a minor axis thereof extending orthogonally to the one direction and a second group of openings each having a substantially oval shape defined by a minor axis thereof extending substantially in parallel to the one direction and a major axis thereof extending orthogonally to the one direction.

Preferably, the topsheet is formed with a plurality of ridges obliquely extending so as to intersect the one direction and protruding from the skin-noncontactable side toward the skin-contactable side.

Alternatively, the plurality of ridges may comprise a first group of ridges and a second group of ridges intersecting the first group of ridges.

According to still another embodiment, the first and second groups of openings comprise those formed in the first and second groups of ridges, respectively, and those formed in regions each defined by a pair of adjacent ridges belonging to the first group and a pair of adjacent ridges belonging to the second group.

The object set forth above is achieved, according to the second aspect of the invention, by a method for making a liquid-permeable topsheet defining at least a part of body fluids absorbent article, the method at least comprising the steps of:

a. continuously feeding a web of thermoplastic synthetic fibers each having a length of 20~70 mm and conveying the web in one direction;

b. directing a high pressure water jet streams onto the web being conveyed so as to entangle the fibers and simultaneously to form first group of liquid-permeable openings each having a major axis thereof extending substantially in parallel to the one direction and a minor axis thereof extending orthogonally to the one direction; and c. subjecting the web formed with the first group of openings to a mechanical treatment so as to form a second group of openings each having a substantially oval shape defined by a minor axis thereof extending substantially in parallel to the one direction and a major axis thereof extending orthogonally to the one direction.

An alternative embodiment of the method may further comprises the step of forming, simultaneously with or after the treatment to form the openings, a plurality of ridges obliquely extending in parallel one to another so as to intersect the one direction in which the web is conveyed and to protrude from one side of the web.

According to still another embodiment of the method, the ridges obliquely extending so as to intersect the direction in which the web is conveyed comprise a first group of ridges extending in parallel one to another and a second group of ridges extending in parallel one to another so as to intersect the first group of ridges.

According to further another embodiment of the method, the mechanical treatment to form said openings may be any one of a embossing treatment and a debossing treatment of said web.

DESCRIPTION OF THE PREFERRED EMBODIMENTS

Figure 1:
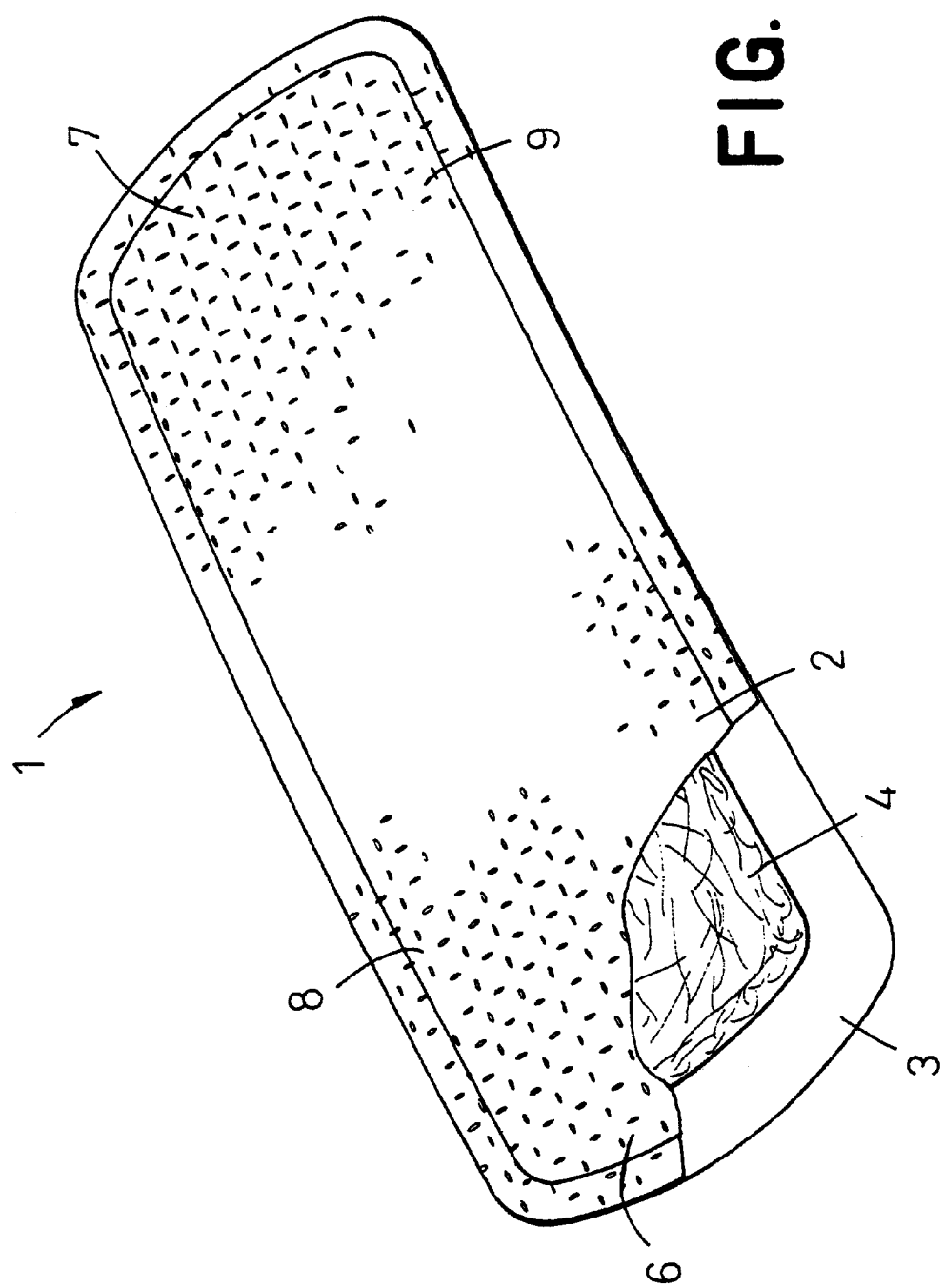
FIG. 1 is a partly cutaway perspective view of a sanitary napkin according to the invention.

FIG. 1 is a partly cutaway perspective view of a sanitary napkin 1 employing a liquid-permeable topsheet 2 according to the invention. The napkin 1 comprises the liquid-permeable topsheet 2, a liquid-impermeable backsheet 3 and a liquid-absorbent core 4 disposed between these two sheets 2, 3. The topsheet 2 and the backsheet 3 are put flat and bonded together along their portions extending outward beyond peripheral edges of the absorbent core 4. The napkin 1 is configured so as to be longitudinally larger and has longitudinally opposite ends 6, 7 and transversely opposite side edges 8, 9.

Figure 2:
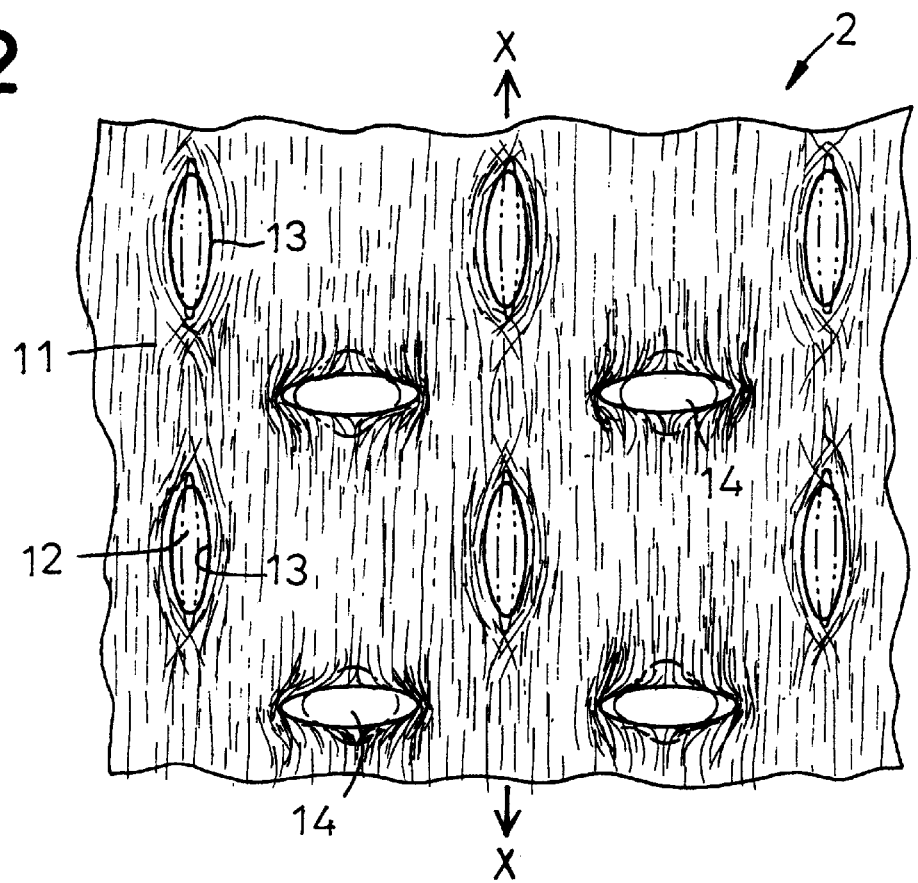
FIG. 2 shows, in enlarged scale, a part of a topsheet of the napkin of FIG. 1 as being pulled in a direction indicated by arrows X.

FIG. 2 shows, in enlarged scale, a part of the topsheet 2. The vertical direction as viewed in this figure corresponds to the longitudinal direction of the napkin 1. The topsheet 2 is formed by a nonwoven fabric made of thermoplastic synthetic fibers 11 each having a fineness of 0.1~10 deniers and a fiber length of 20~70 mm. To obtain the nonwoven fabric, a web comprising the thermoplastic synthetic fibers 11 and having a basis weight of 10~50 g/m$^2$ is subjected to water jet streams of a high pressure so that the fibers 11 may be mechanically entangled and a plurality of first openings 12 larger than interstices among each of the entangled fibers 11 may be simultaneously formed. In the topsheet 2, the fibers 11 extend substantially in the longitudinal direction of the napkin 1.

Each of first openings 12 has a substantially oval shape defined by a major axis extending toward the longitudinally opposite ends 6, 7 and a minor axis extending toward the transversely opposite side edges 8, 9, i.e., orthogonally to the major axis. In the proximity of the first opening 12, the fibers 11 extend longitudinally of the napkin 1 along side edges 13 of each of the openings 12.

The topsheet 2 additionally has a plurality of second openings 14 each presenting a substantially oval shape defined by a major axis extending toward the transversely opposite side edges 8, 9 and a minor axis extending toward the longitudinally opposite ends 6, 7. The second openings 14 are formed by using an embossing tool provided with a plurality of projections each contoured substantially in conformity with the opening 14. More specifically, the nonwoven fabric is pierced by the projections. More preferably, the nonwoven fabric is pierced by the projections which are heated so that the constituent fibers 11 of the nonwoven fabric may be thermally formed substantially in conformity with the openings 14.

In the topsheet 2, the first and second openings 12, 14 have their major axes dimensioned to be 0.7~7 mm and their minor axes preferably dimensioned to be less than ½ of the dimension of the major axes, i.e., 0.35~3.5 mm. Substantially total quantity of body fluids discharged onto the topsheet 2 transfers through the first and second openings 12, 14 to the absorbent core 4. While portions of the nonwoven fabric surrounding the openings 12, 14 includes numerous fiber interstices, the interstices are substantially smaller than the openings 12, 14 and a quantity of body fluids transferring through these interstices is negligibly small compared to the quantity passing through the openings 12, 14. It should be understood that the thermoplastic synthetic fibers may be also treated to become hydrophilic before it is finally formed as the topsheet, if desired.

The backsheet 3 is preferably formed by a liquid-impermeable plastic film, and more preferably formed by a breathable but liquid-impermeable plastic film. If desired, a nonwoven fabric may be laminated on an outer surface of the film to form the backsheet 3.

The absorbent core 4 may be formed by fluff pulp or a mixture of fluff pulp and polymer powder of high water absorptivity.

With the napkin 1 of the above-mentioned construction, the first opening 12 has its dimension as measured longitudinally of the napkin 1 enlarged as the topsheet 2 is pulled in the direction indicated by the arrows X (i.e., toward the longitudinally opposite ends 6, 7 thereof). On the other hand, the first opening 12 has its dimension as measured transversely of the napkin 1 correspondingly reduced, sometimes preventing body fluids from flowing into the first opening 12. While the second opening 14 also has its dimension as measured longitudinally of the napkin 1, its dimension as measured transversely of the napkin 1 is not too reduced to prevent body fluids from flowing into the second opening 14.

Figure 3:
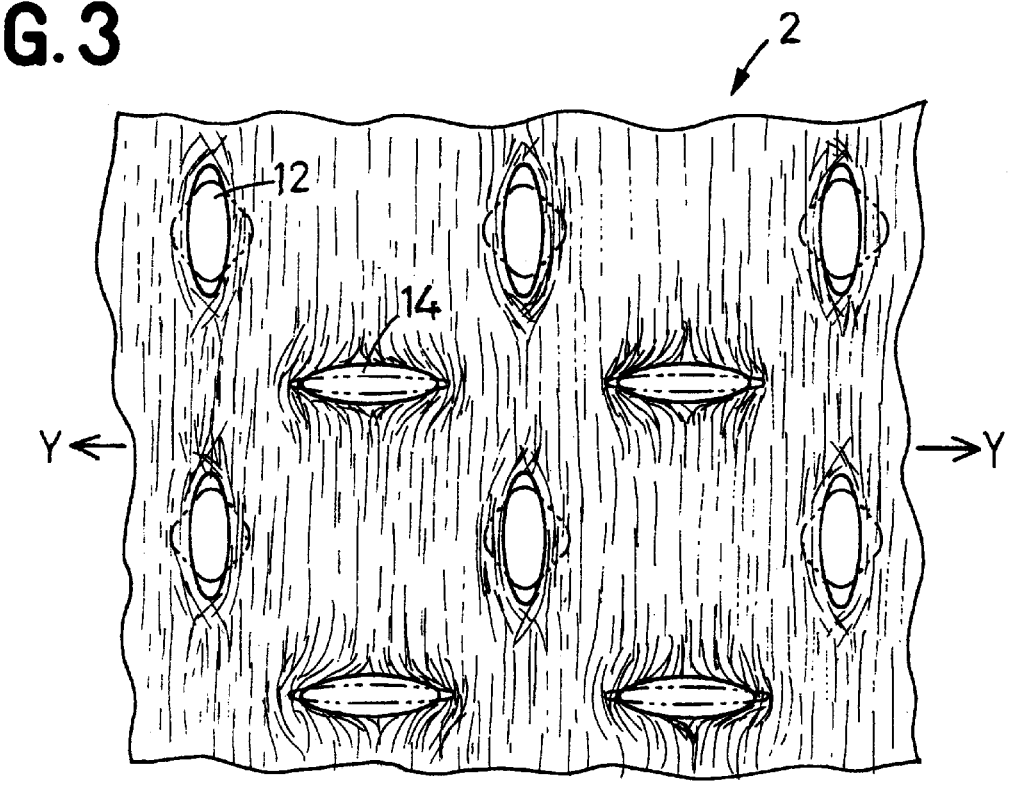
FIG. 3 is a view similar to FIG. 2 of the same part of the topsheet as being pulled in a direction indicated by arrows Y.

FIG. 3 is a view similar to FIG. 2 showing how the first and second openings 12, 14 are deformed as the topsheet 2 is pulled toward the transversely opposite side edges 8, 9, i.e., in the direction indicated by the arrows Y. As shown, the first opening 12 is not so significantly deformed to prevent body fluids from flowing thereinto. On the other hand, the second opening 14 has its dimension as measured transversely of the napkin 1 enlarged and its dimension as measured longitudinally of the napkin 1 is further reduced, sometimes preventing body fluids from flowing thereinto.

It will be apparent from the behavior of the topsheet 2 as illustrated by FIGS. 2 and 3, body fluids discharged on to the topsheet 2 can rapidly transfer through the first or second openings 12, 14 to the absorbent core 4, depending on the direction in which the napkin 1 is pulled. In this manner, rapid transfer body fluids from the topsheet 2 to the absorbent core 4 is reliably assured.

Figure 4:
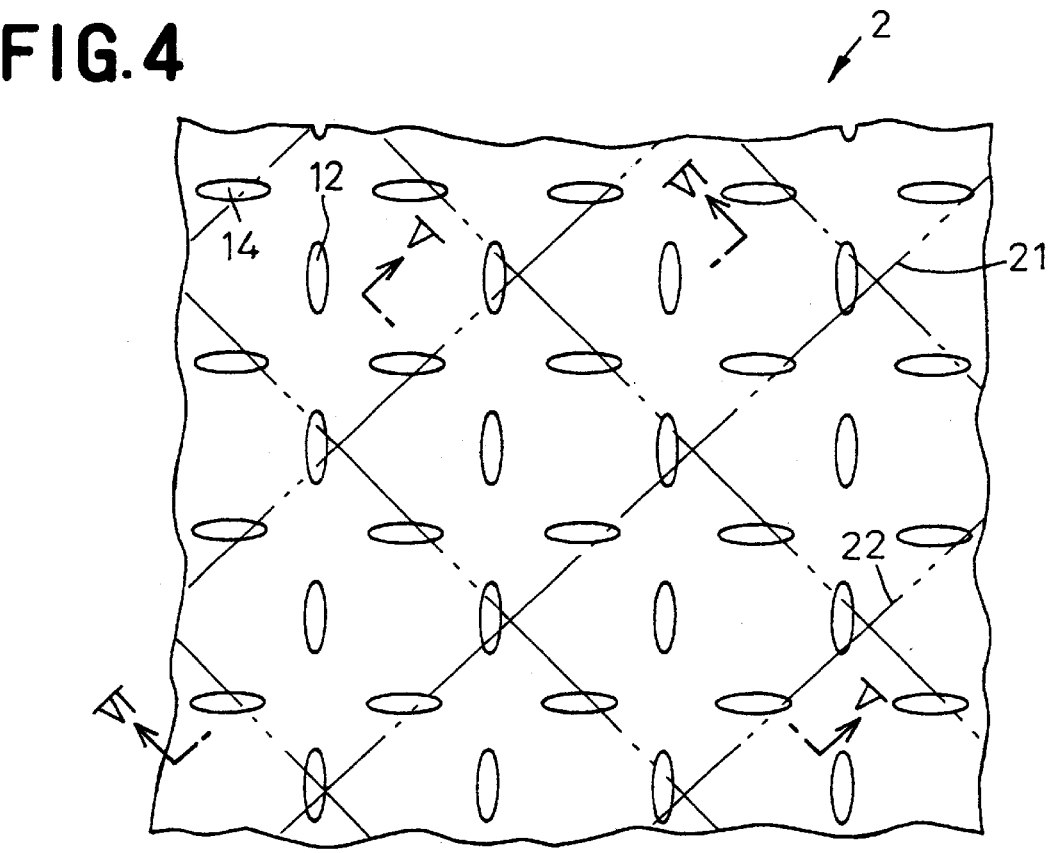
FIG. 4 is a view similar to FIG. 2 of a variant of the invention.
Figure 5:
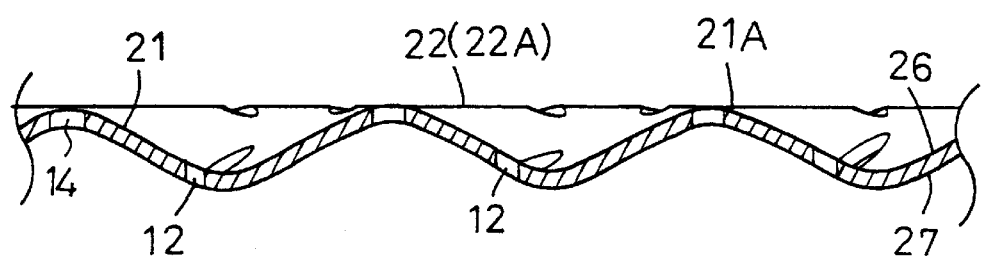
FIG. 5 is a sectional view taken along line V—V in FIG. 4.
Figure 6:
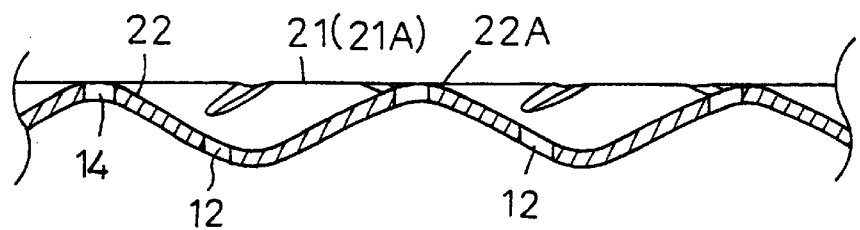
FIG. 6 is a sectional view taken along line VI—VI in FIG. 4.

FIGS. 4, 5 and 6 are respectively a fragmentary plan view similar to FIG. 2 showing a variant of the invention, a sectional view thereof taken along line V—V and a sectional view thereof taken along line VI—VI both in FIG. 4. It should be understood that the fibers 11 are not shown in these figures. The topsheet 2 according to this variant is formed with a plurality of first ridges 21 extending obliquely upward from left to right as viewed in FIG. 4 in parallel one to another. The topsheet 2 is formed also with a plurality of second ridges 22 extending obliquely downward from right to left as viewed in FIG. 4. Imaginary lines indicate respective crests 21A, 22A of the ridges 21, 22. The topsheet 2 has a skin-contactable side 26 intended to come in contact with the wearer's skin and a skin-noncontactable side 27 intended not to come in contact with the wearer's skin when the napkin 1 is worn. As viewed in the transverse section of the ridges 21, 22, the side 27 is configured so as to come in contact with the wearer's skin (not shown) at the crests 21A, 22A. The first and second openings 12, 14 are distributed not only on the ridges 21, 22 but also in the regions each defined by a pair of adjacent first ridges 21 and a pair of adjacent second ridges 22 crossing the pair of adjacent first ridges 21. The ridges 21, 22 have a substantially uniform height of 0.2~2 mm, preferably of 0.3~1.5 mm. Both each pair of adjacent ridges 21 and each pair of adjacent second ridges 22 are preferably spaced from each other by a crest-to-crest distance of 2~7 mm, respectively. The presence of the first and second openings 12, 14 as well as the first and second ridges 21, 22 gives the topsheet 2 shown by FIGS. 4–6 an appearance characterized by fine irregularities and openings like knitted goods. Such an appearance is quite different from that of an ordinary flat nonwoven fabric. It should be understood that the rid formed on the topsheet 2 may comprise only one group of the first and second ridge groups 21, 22.

Figure 7:
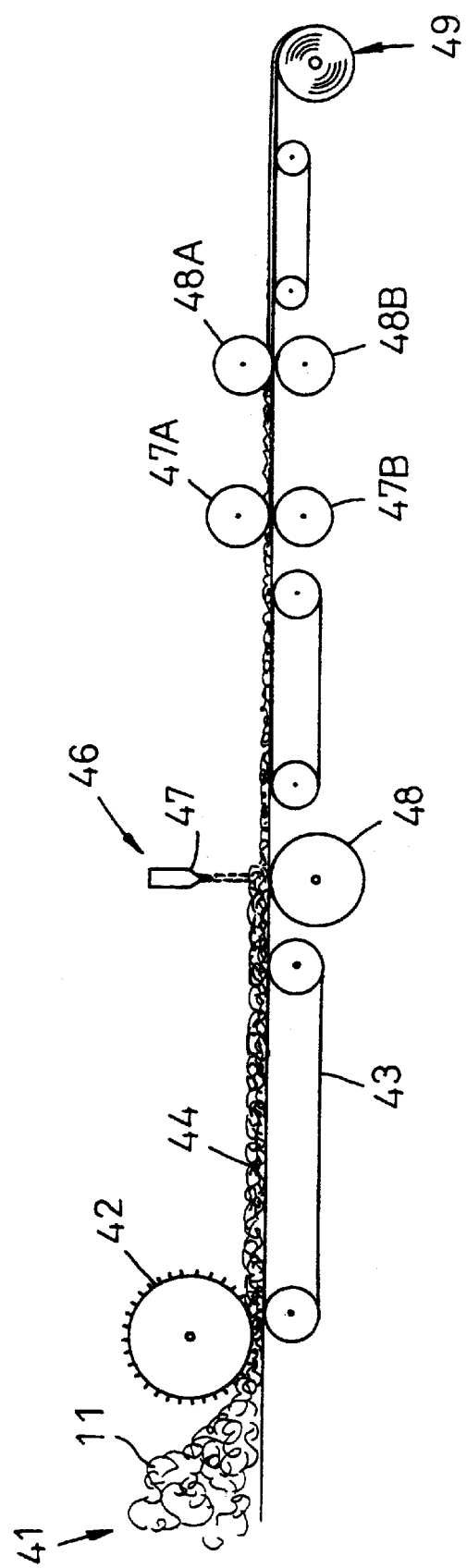
FIG. 7 is a diagram illustrating steps for making the topsheet.
Figure 8:
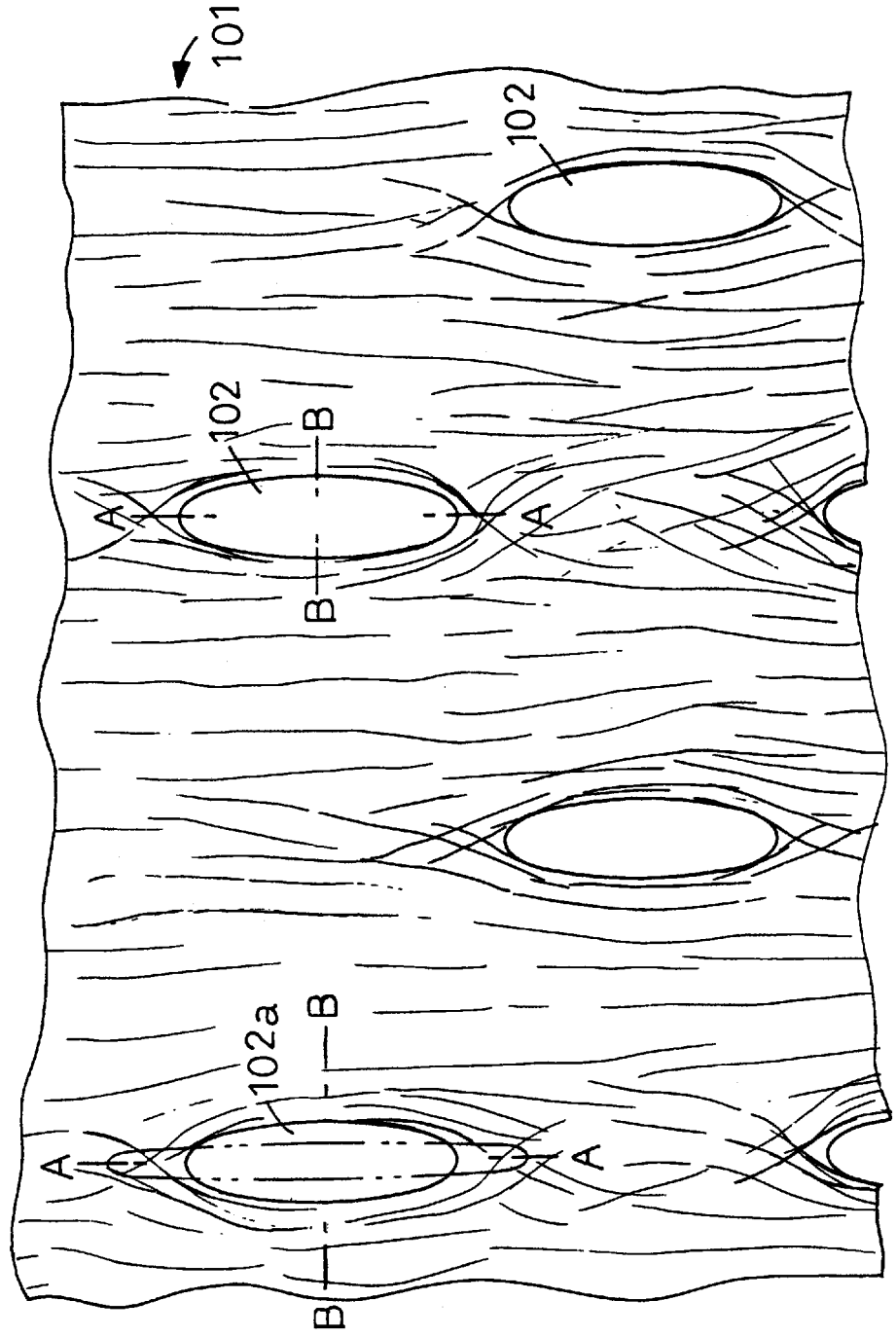
FIG. 8 is a plan view of the topsheet of prior art.

FIG. 7 is a diagram illustrating the steps for making the topsheet 2 shown by FIG. 4. Thermoplastic synthetic staple fibers 41 are treated by a combing roll 42 to form a web 44 which is conveyed by an endless belt 43 to a high pressure water jet apparatus 46. The apparatus 46 comprises jet nozzle means 47 having a plurality of articles and a solid molding roll 48. The roll 48 having a plurality of projections (not shown) distributed thereon in a desired pattern so that the fibers of the web are rearranged about a periphery of each of the projections under pressure of the water jets and thereby each of the first openings 12 is formed substantially in conformity with the periphery of each of the projections. Each of the projections has its major axis being aligned with the direction in which the web 44 travels. Having been treated by the apparatus 46, the web 44 takes a form of nonwoven fabric composed of the entangled fibers and having a plurality of the first openings 12. Then the web 44 passes between a pair of first embossing rolls 47A, 47B and thereby the second openings 14 are mechanically formed. The web 44 then passes between a pair of second embossing rolls 48A, 48B and thereby the first and second ridge groups 21, 22 are formed. The treatment by the first and second embossing roll pairs 47A, 47B; 48A, 48B is preferably carried out at an intermediate temperature between the normal room temperature and a temperature corresponding to the melting point, more preferably at a temperature substantially corresponding to a softening temperature of the web 44. After embossing treatment, the web 44 is taken up in the form of a roll and cut into appropriate dimension to be used as the topsheet 2. The steps for making the topsheet 2 may be modified so as to form the second openings 14 as well as the first and second ridge groups 21, 22 simultaneously by a single step of embossing treatment. It is also possible to replace at least one of the first and second embossing roll pairs 47A, 47B; 48A, 48B by a debossing roll pair.

The topsheet according to the invention used in body fluids absorbent article comprises the first openings each substantially in oval shape having its major axis extending in a given direction and the second openings each substantially in oval shape having its major axis extending orthogonally to the given direction. With such an unique arrangement, a desired liquid-permeability of the topsheet can be maintained by the first openings or the second openings, depending on whether the topsheet is pulled in the, given direction or in the direction orthogonal to the given direction.

With the embodiment of the topsheet having a plurality of ridges, the ridges cooperate with the presence of the first and second openings to give the topsheet an outer appearance like the knitted goods.

What is claimed is:

1. A method for making a liquid-permeable topsheet for use in forming at least a part of body fluids absorbent article, said method comprising the steps of:
   a. continuously feeding a web of thermoplastic synthetic fibers each having a length of about 20 to about 70 mm and conveying the web in one direction;
   b. directing high pressure water jet streams onto said web so as to entangle said fibers and simultaneously form a first group of liquid-permeable openings in the web with each opening having a major axis that extends substantially in parallel to said one direction and a minor axis that extends orthogonally to said one direction; and
   c. subjecting the web formed with said first group of openings to a mechanical process which forms a second group of openings in the web with each opening having a substantially oval shape defined by a minor axis that extends substantially in parallel to said one direction and a major axis that extends orthogonally to said one direction.

2. The method according to claim 1, further comprising the step of forming a plurality of parallel ridges in said web which extend obliquely with respect to said one direction in which said web is conveyed and which protrude from one side of said web.

3. The method according to claim 2, wherein said ridges comprise a first group of ridges extending in parallel one to another and a second group of ridges extending in parallel one to another so as to intersect said first group of ridges.

4. The method according to claim 1, wherein said mechanical process used to form said openings comprises a embossing process.

5. The method according to claim 1, wherein said mechanical process used to form said openings comprises a debossing process.

6. The method according to claim 2, wherein the step of forming the plurality of parallel ridges occurs substantially simultaneously with the step of forming the second group of openings.

7. The method according to claim 1, wherein the step of forming the plurality of parallel ridges occurs after the step of forming the second group of openings.

* * * * *